(12) United States Patent
Zhang et al.

(10) Patent No.: US 8,653,281 B2
(45) Date of Patent: Feb. 18, 2014

(54) PROCESS FOR THE MANUFACTURE OF AGOMELATINE AND ITS INTERMEDIATE

(75) Inventors: Guisen Zhang, Xuzhou (CN); Daopeng Chen, Xuzhou (CN); Yanqin Ma, Xuzhou (CN); Xiangping Yang, Xuzhou (CN); Shixia Zhou, Xuzhou (CN); Liang Chen, Xuzhou (CN)

(73) Assignee: NHWA Pharma. Corporation (CN)

( * ) Notice: Subject to any disclaimer, the term of this patent is extended or adjusted under 35 U.S.C. 154(b) by 147 days.

(21) Appl. No.: 13/056,032

(22) PCT Filed: Jul. 23, 2009

(86) PCT No.: PCT/CN2009/072886
§ 371 (c)(1),
(2), (4) Date: Jan. 26, 2011

(87) PCT Pub. No.: WO2010/012208
PCT Pub. Date: Feb. 4, 2010

(65) Prior Publication Data
US 2011/0130571 A1 Jun. 2, 2011

(30) Foreign Application Priority Data
Jul. 29, 2008 (CN) .......................... 2008 1 0020827

(51) Int. Cl.
*C07D 209/48* (2006.01)
(52) U.S. Cl.
USPC ........................................ 548/473

(58) Field of Classification Search
USPC ........................................ 548/473
See application file for complete search history.

(56) References Cited

FOREIGN PATENT DOCUMENTS

EP          0447285 A1   9/1991
WO    WO 2005/077888 A1   8/2005

OTHER PUBLICATIONS

Depreux et al. "Synthesis and Structure—Activity Relationships of Novel Naphthalenic and Bioisosteric Related Amidic Derivatives as Melatonin Receptor Ligands", *J. Med. Chem.* 37:3231-3239 (1994).
Leclerc et al. "Synthesis and Structure—Activity Relationships of Novel Naphthalenic and Bioisosteric Related Amidic Derivatives as Melatonin Receptor Ligands", *Bioorganic & Medicinal Chemistry* 6:1875-1887 (1998).
International Search Report corresponding to International Application No. PCT/CN2009/072886 mailed Oct. 29, 2009.

*Primary Examiner* — Shawquia Young
(74) *Attorney, Agent, or Firm* — Myers Bigel Sibley & Sajovec, P.A.

(57) ABSTRACT

A process for the manufacture of agomelatine and its intermediate N-[2-(7-methoxy- 1-naphthy)ethyl]phthalimide is provided and inclues reacting 7-methoxy-1-naphthyl ethanol (III) with benzenesulfonyl chloride to obtain 7-methoxy-1-naphthylethyl benzene sulfonate (IV), which is reacted with potassium phthalimide to produce N-[2-(7-methoxy-1-naphthy)ethyl]phthalimide (II); and subjecting N-[2-(7-methoxy-1-naphthy)ethyl]phthalimide (II) to alkaline hydrolysis and acetylation, to obtain agomelatine.

23 Claims, No Drawings

PROCESS FOR THE MANUFACTURE OF AGOMELATINE AND ITS INTERMEDIATE

RELATED APPLICATIONS

This application is a 35 U.S.C. §371 national stage application of PCT Application No. PCT/CN2009/072886, filed on Jul. 23, 2009, which claims priority from Chinese Application No. 2008-1020827.3 filed Jul. 29, 2008, the contents of which are incorporated herein by reference in their entireties. The above-referenced PCT International Application was published as International Publication No. WO 2010/012208 A1 on Feb. 4, 2010.

FIELD OF THE INVENTION

The invention relates to a process for the manufacture of agomelatine, also to an intermediate used in the process and its manufacturing process.

BACKGROUND OF THE INVENTION

Agomelatine, N-[2-(7-methoxy-1-naphthyl)ethyl]acetamide, is a melatonin receptor agonist, and is a new antidepressant and antianxiety drug. EP0447285 discloses the chemical structure of agomelatine, and the use of agomelatine as an antianxiety drug, an antidepressant, and an antipsychotic drug. Agomelatine has a chemical structure represented by formula (I).

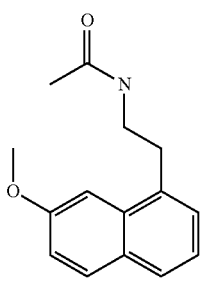

A number of methods for the synthesis of agomelatine have been reported, and they can generally be divided into two types, which both use 7-methoxy-1-tetralone as a starting material. The first type of methods are described in the literatures such as EP0447285, 1992. JMC, and 1994. JMC. (see reaction scheme I).

Reaction Scheme I:

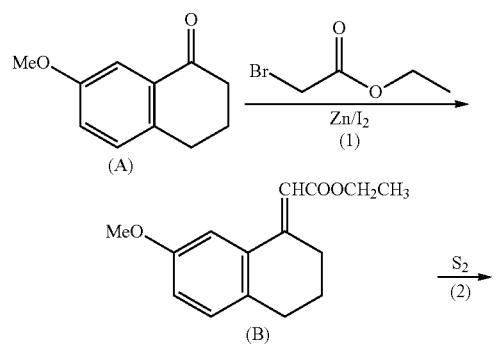

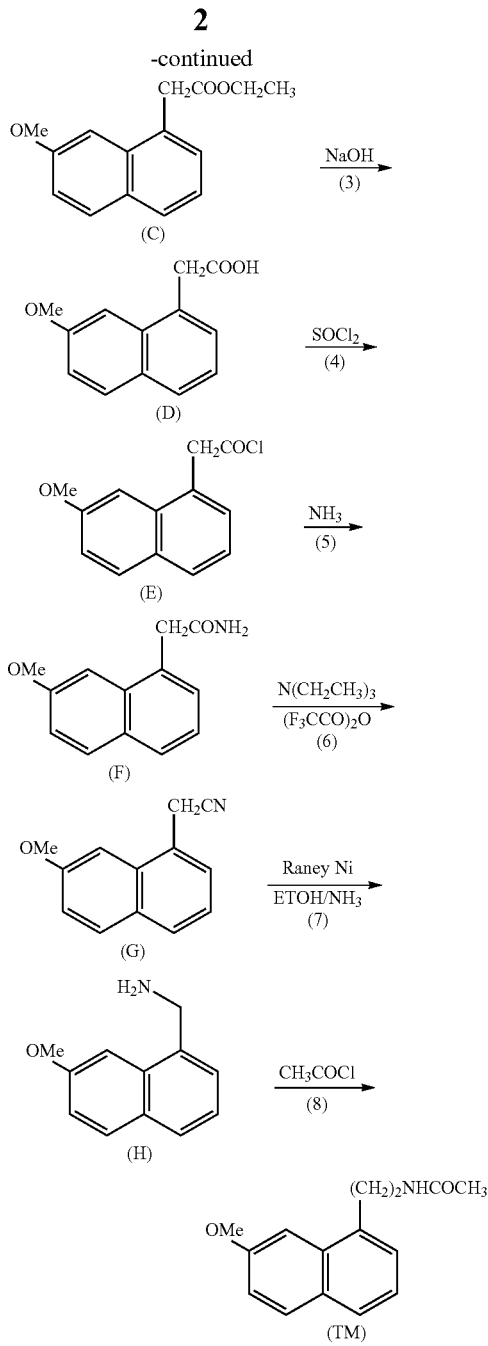

The disadvantages of this type of methods lie in that many steps are involved; the reaction in the first step is found to be poorly reproducible; compound (B) often goes through an incomplete aromatization in step (2) and the reactions in the subsequent steps do not usually go to complete either; purification of the mixture obtained in the saponification of step (3) is so difficult that column chromatography is necessitated; the hydrogenation pressure in step (7) is as high as 300 atm, as reported in the relevant patents, and it is difficult to generate such a high pressure in the industrial production; and the average total yield is lower than 30%.

The second type of methods are described in the literatures such as US2005/0182276 and Synthetic Communication 2001, 31(4), 321-629 (see reaction scheme II).

Reaction Scheme II

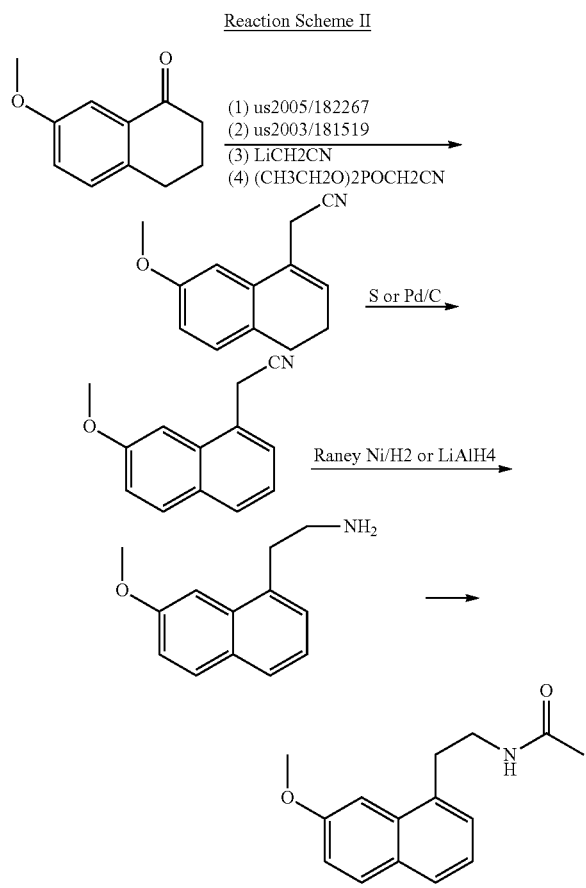

The advantages of this type of methods lie in that two carbon atoms and one nitrogen atom of the target molecule are introduced in the first step, and transformed into a target functional group through hydrogenation, which is desirable from an economic viewpoint; the intermediates can be readily separated and purified, and a single recrystallization gives the target product with a purity of 99%. However, the methods have the disadvantage that the hydrogenation of a cyano group also requires a high pressure of 300 atm, which is difficult to be generated in the industrial production.

Furthermore, 7-methoxy-1-tetralone used in those two types of methods as the starting material, is costly and not easily available.

In view of the above problems occurred in those methods for the synthesis of agomelatine, there remains a need for a new process for the manufacture of agomelatine, which uses easily available and inexpensive materials, is convenient and simple, and can be easily performed on an industrial scale.

SUMMARY OF THE INVENTION

It is an object of the invention to provide a new process for the manufacture of N-[2-(7-methoxy-1-naphthyl)ethyl]acetamide (also known as agomelatine), which overcomes the disadvantages of the prior art methods.

According to one aspect of the invention, there is provided N-[2-(7-methoxy-1-naphthyl)ethyl]phthalimide of formula II.

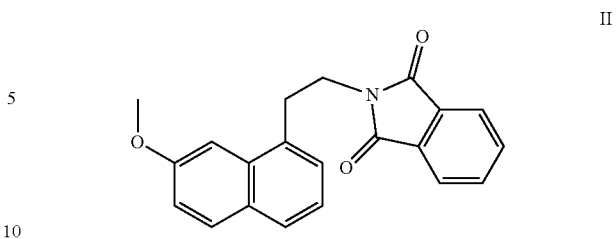

According to another aspect of the invention, there is provided a process for the manufacture of N-[2-(7-methoxy-1-naphthyl)ethyl]phthalimide of the above formula II, which comprises the step of reacting 7-methoxy-1-naphthylethyl alkyl- or aryl-sulfonate, where the alkyl is a linear or branched $C_1$-$C_6$ alkyl, and the aryl is a $C_5$-$C_6$ aryl unsubstituted or substituted by a linear or branched $C_1$-$C_6$ alkyl or a linear or branched $C_1$-$C_6$ alkoxy, with potassium phthalimide in a polar aprotic solvent.

According to still another aspect of the invention, there is provided a process for the manufacture of 2-(7-methoxy-1-naphthyl)ethyl amine or its salts, which comprises the steps of alkaline hydrolysis of N-[2-(7-methoxy-1-naphthyl)ethyl] phthalimide, and optionally conversion of the obtained amine into a salt with an acid such as a solution of hydrogen chloride in ethyl acetate.

According to yet still another aspect of the invention, there is provided a process for the manufacture of agomelatine, which comprises the following steps:
1) N-[2-(7-methoxy-1-naphthyl)ethyl]phthalimide is subjected to alkaline hydrolysis in a linear or branched $C_1$-$C_4$ alkanol, to give 2-(7-methoxy-1-naphthyl)ethylamine, which is optionally converted into a salt with an acid;
2) 2-(7-methoxy-1-naphthyl)ethylamine or its salt is reacted with an acylating agent, to give agomelatine.

PREFERRED EMBODIMENTS OF THE INVENTION

In the present invention, N-[2-(7-methoxy-1-naphthyl)ethyl]phthalimide of formula II is a critical intermediate in the manufacture of agomelatine.

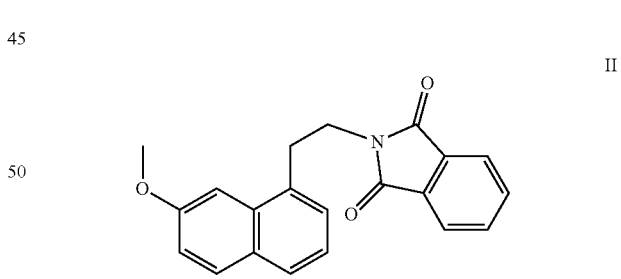

The process for the manufacture of N-[2-(7-methoxy-1-naphthyl)ethyl]phthalimide according to the invention comprises the step of reacting 7-methoxy-1-naphthylethyl alkyl- or aryl-sulfonate, where the alkyl is a linear or branched $C_1$-$C_6$ alkyl, and the aryl is a $C_5$-$C_6$ aryl unsubstituted or substituted by a linear or branched $C_1$-$C_6$ alkyl or a linear or branched $C_1$-$C_6$ alkoxy, with potassium phthalimide in a polar aprotic solvent. In the process, the polar aprotic solvent may be, for example, dimethylformamide or acetonitrile.

The 7-methoxy-1-naphthylethyl alkyl- or aryl-sulfonate is prepared by reacting 7-methoxy-1-naphthyl ethanol with a corresponding alkyl- or aryl-sulfonyl halide, where the alkyl is a linear or branched $C_1$-$C_6$ alkyl, and the aryl is a $C_5$-$C_6$ aryl unsubstituted or substituted by a linear or branched $C_1$-$C_6$ alkyl or a linear or branched $C_1$-$C_6$ alkoxy, in an aprotic solvent in the presence of a base. The aprotic solvent may be, for example, a partially or fully chlorinated $C_1$-$C_6$ alkane, or pyridine, preference being given to dichloromethane, dichloroethane, chloroform, or carbon tetrachloride. The reaction temperature may be in the range from −10° C. to room temperature.

The alkyl is, for example, methyl, ethyl, n-propyl, isopropyl, n-butyl, tert-butyl, n-pentyl and n-hexyl, preferably $C_1$-$C_4$ alkyl, and more preferably methyl and ethyl. The aryl is preferably phenyl unsubstituted or substituted by a linear or branched $C_1$-$C_4$ alkyl or a linear or branched $C_1$-$C_4$ alkoxy, and more preferably phenyl or p-tolyl.

In the preparation of the 7-methoxy-1-naphthylethyl alkyl- or aryl-sulfonate, the sulfonyl halide used is a sulfonyl chloride, preferably $C_1$-$C_4$ alkylsulfonyl chloride, or benzenesulfonyl chloride unsubstituted or substituted by a linear or branched $C_1$-$C_6$ alkyl or a linear or branched $C_1$-$C_6$ alkoxy, more preferably methylsulfonyl chloride, ethylsulfonyl chloride, benzenesulfonyl chloride unsubstituted or substituted by a linear or branched $C_1$-$C_4$ alkyl or a linear or branched $C_1$-$C_4$ alkoxy, and more particularly preferably benzenesulfonyl chloride or p-toluenesulfonyl chloride.

The base is selected from $NR_3$, where R may be identical or different and represents H or a linear or branched $C_1$-$C_4$ alkyl, with a proviso that all the R groups are not simultaneously H, or pyridine. The base is preferably selected from diethyl amine, dipropyl amine, dibutyl amine, triethyl amine, tripropyl amine, tributyl amine, or pyridine, and more preferably is diethyl amine, triethyl amine, or pyridine.

The process for the manufacture of N-[2-(7-methoxy-1-naphthyl)ethyl]phthalimide according to the invention can take place according to the following scheme, starting with, for example, an alkyl- or aryl-sulfonyl chloride.

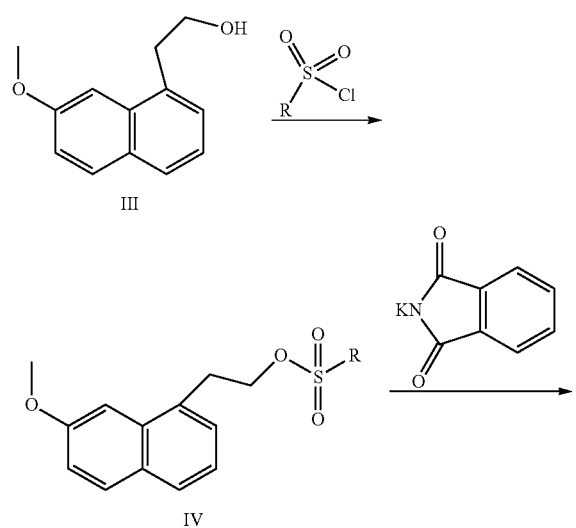

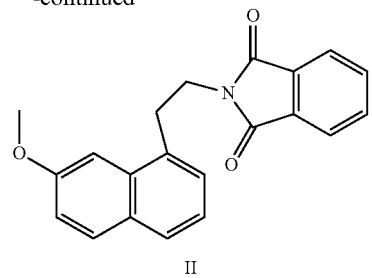

R = an alkyl, or an unsubstituted or substituted aryl

R=an alkyl, or an unsubstituted or substituted aryl

In the process, 7-methoxy-1-naphthyl ethanol (III) is reacted with an alkyl- or aryl-sulfonyl chloride in a molar ratio of 1:1-10, preferably 1:2-6, more preferably 1:2-5, in a lower alcohol such as methanol and/or ethanol, to obtain 7-methoxy-1-naphthylethyl alkyl- or aryl-sulfonate (IV). The reaction temperature is in the range from −10° C. to room temperature, preferably from −10° C. to 10° C., more preferably from −10° C. to 0° C.

Subsequently, the obtained 7-methoxy-1-naphthylethyl alkyl- or aryl-sulfonate (IV) is reacted with potassium phthalimide in a polar aprotic solvent, to produce N-[2-(7-methoxy-1-naphthyl)ethyl]phthalimide (II). The polar aprotic solvent is selected from dimethylformamide and acetonitrile, and is preferably dimethylformamide. The molar ratio of 7-methoxy-1-naphthylethyl alkyl- or aryl-sulfonate (IV) and potassium phthalimide is 1:1-2, preferably 1:1-1.6, more preferably 1:1.1-1.5.

The invention also provides a process for the manufacture of 2-(7-methoxy-1-naphthyl)ethylamine or its salt, comprising the steps of alkaline hydrolysis of N-[2-(7-methoxy-1-naphthyl)ethyl]phthalimide, and optionally conversion of the obtained amine into a salt with an acid such as a solution of hydrogen chloride in ethyl acetate.

The process for the manufacture of agomelatine according to the invention comprises the following steps:

1) N-[2-(7-methoxy-1-naphthyl)ethyl]phthalimide is subjected to alkaline hydrolysis in a linear or branched $C_1$-$C_4$ alkanol, to give 2-(7-methoxy-1-naphthyl)ethylamine, which is optionally converted into a salt with an acid;
2) 2-(7-methoxy-1-naphthyl)ethylamine or its salt is reacted with an acetylating agent such as acetic anhydride or acetyl chloride, to produce agomelatine.

In the process for the manufacture of agomelatine according to the invention, the alkanol used is selected from methanol, ethanol, isopropanol, n-butanol, or a combination thereof. The alkali used in the alkaline hydrolysis is selected from alkali metal hydroxide, alkaline-earth metal hydroxide, or hydrazine hydrate, and is preferably sodium hydroxide, potassium hydroxide, or hydrazine hydrate.

After the alkaline hydrolysis, the obtained hydrolyzate is purified by extraction with a nonpolar organic solvent, the solvent being preferably a partially or fully chlorinated $C_1$-$C_6$ alkane, or ethyl acetate, and more preferably selected from dichloromethane, dichloroethane, chloroform, carbon tetrachloride, and ethyl acetate.

The process for the manufacture of agomelatine according to the invention can take place according to the following scheme.

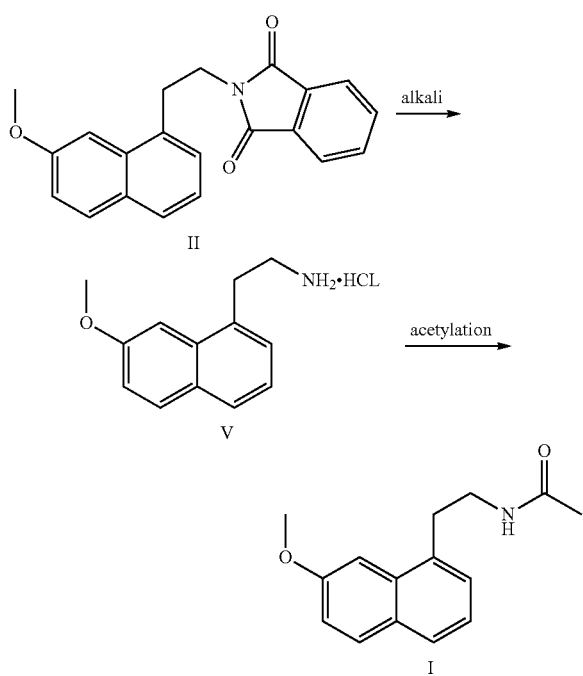

2-(7-methoxy-1-naphthyl)ethylamine hydrochloride (V) is obtained by subjecting N-[2-(7-methoxy-1-naphthyl)ethyl]phthalimide to alkaline hydrolysis in a lower alcohol, followed by extraction with an acid, neutralization with a base, and extraction with a nonpolar solvent, and reacting with HCl/ethyl acetate. The acid used for the extraction is selected from a dilute inorganic acid, preferably dilute hydrochloric acid and dilute sulfuric acid, and more preferably dilute hydrochloric acid. The base used for the neutralization is selected from alkali metal hydroxide, preferably sodium hydroxide, potassium hydroxide, and more preferably sodium hydroxide. The nonpolar solvent used for the extraction is selected from chloroalkane or ethyl acetate, preferably dichloromethane, dichloroethane, chloroform, carbon tetrachloride, or ethyl acetate, and more preferably dichloromethane, dichloroethane, or ethyl acetate.

The obtained 2-(7-methoxy-1-naphthyl)ethylamine hydrochloride (V) is then reacted with an acetylating agent. The reaction product is extracted with a nonpolar solvent, and the extract is dried and concentrated, thereby giving a crude agomelatine product, which is recrystallized in a mixed solvent of toluene and n-hexane with a certain ratio, to produce agomelatine. The nonpolar solvent used for the extraction is selected from chloroalkane or ethyl acetate, preferably dichloromethane, dichloroethane, chloroform, carbon tetrachloride, or ethyl acetate, and more preferably dichloromethane, dichloroethane, or ethyl acetate. The volume ratio of toluene and n-hexane for the recrystallization is 2:1.

The process for the manufacture of agomelatine according to the invention provides for a number of advantages. The synthesis route is short, and a small number of reaction steps are involved in the process (a four-step reaction leads to a target product starting from 7-methoxy-1-naphthyl ethanol (III)). The process according to the invention is convenient and simple, while not requiring distillation and separation by column chromatography. The reaction condition for each step is mild, and no harsh conditions including high temperature, high pressure, high vacuum, are necessary. No special equipment (for example, a high-pressure hydrogenation reactor) needs to be used. The separation and purification of the intermediates are easy to perform, and the materials and reagents used in the process are commercially available. A final product with a good purity can be obtained by the process according to the invention. In addition, the process according to the invention is suitable for industrial use.

The following examples are used to illustrate the invention, but are not intended to limit the invention in any way.

All materials and reagents used in the invention are commercially available. Below are the sources of the main materials and reagents:

7-methoxy-1-naphthyl ethanol, available from Xuzhou Bestenchem Technology Company Ltd.;
benzenesulfonyl chloride, available from Jiaxing Jinhe Chemical Corporation Ltd.;
hydrazine hydrate, available from Shanghai Zhongsheng Chemical Corporation Ltd.;
potassium phthalimide, available from Zibo Libang Fine Chemical Company Ltd.;
acetic anhydride, available from Shanghai Lingfeng Chemical Reagent Company Ltd.;
acetyl chloride, available from Xuzhou Bestenchem Technology Company Ltd.;
diethyl amine, triethyl amine, and pyridine, available from Shanghai Chemical Reagent Company, China Pharmaceutical Group.

Example 1

Preparation of N-[2-(7-methoxy-1-naphthyl)ethyl]phthalimide (II)

1) Synthesis of 7-methoxy-1-naphthylethyl Benzene Sulfonate 7.7 g of 7-methoxy-1-naphthyl ethanol (III, 7.7 g, 0.038 mol) was dissolved in 80 ml of pyridine, and a solution of benzenesulfonyl chloride (13.5 g, 0.076 mol) in pyridine was added dropwise over about one hour at −10° C. A reaction at a temperature of from −10° C. to −5° C. was allowed to proceed for 3 hours. The reaction solution was then poured into 150 g of ice water with stirring, and extracted with toluene (80 ml*3). The organic phases were combined, washed with water (200 ml*3), dried with magnesium sulfate, filtered to remove the drying agent, and concentrated under reduced pressure, to give an oil residue. The residue was recrystallized in methanol (80 ml), to produce 9.1 g of 7-methoxy-1-naphthylethyl benzene sulfonate (IV). The yield was 70%. The melting point was 86-87° C.

IR $\bar{v}_{cm^{-1}}$: 1362, 1184.92, 1624.97, 1599, 1511, 1471
$^1$HNMR (CDCl$_3$) δ: 7.20 (d, 1H, J=2.4 Hz), 7.14 (dd, 1H, J=8.8, 2.4 Hz), 7.73 (d, 1H, J=8.8 Hz), 7.66 (dd, 1H, J=7.6, 2.0 Hz), 4.36 (t, 2H, J=7.6 Hz), 3.92 (s, 3H), 3.44 (t, 2H, J=7.6 Hz)
MS: m/z 342 (M+1)

2) Synthesis of N-[2-(7-methoxy-1-naphthyl)ethyl]phthalimide (II)

The compound IV (14 g, 0.041 mol) produced as described above and potassium phthalimide (8.3 g, 0.045 mol) were added into a flask containing dimethylformamide (180 ml) as a solvent, heated and refluxed for 2 hours. After cooling the content to room temperature, 200 ml of water was added. The mixture was stirred and filtered. The filter cake formed was washed with water and dried, to produce 10.8 g of N-[2-(7- methoxy-1-naphthyl)ethyl]phthalimide (II). The yield was 80%. The melting point was 159-160° C.

IR $\bar{v}_{cm-1}$: 1766.90, 1701.51 (C=O), 1329.46 (C—N)

$^1$HNMR (CDCl$_3$) δ: 7.85-7.90 (br, 2H), 7.68-7.79 (br, 5H), 7.41 (d, 1H, J=7.2 Hz), 7.28 (d, 1H, J=7.2 Hz), 4.1 (s, 3H), 4.02 (t, 2H, J=8.8 Hz), 3.38 (t, 2H, J=8.8 Hz)

MS: m/z 331 (M+1)

Example 2

Preparation of
N-[2-(7-methoxy-1-naphthyl)ethyl]phthalimide (II)

1) Synthesis of 7-methoxy-1-naphthylethyl Benzene Sulfonate (IV)

7-methoxy-1-naphthyl ethanol (III, 7.7 g, 0.038 mol) was dissolved in 100 ml of dichloromethane, and diethyl amine (5 ml) was added, and a solution of benzenesulfonyl chloride (33.6 g, 0.19 mol) in dichloromethane was added dropwise over about one hour at 0° C. A reaction at a temperature of from 0° C. to 5° C. was allowed to proceed for 3 hours. The reaction solution was then poured into 150 g of ice water with stirring, and extracted with dichloromethane (20 ml*3). The organic phases were combined, washed with water (100 ml*3), dried with magnesium sulfate, filtered to remove the drying agent, and concentrated under reduced pressure, to give an oil residue. The residue was recrystallized in a 1:1 methanol/ethanol mixture (90 ml), to produce 11 g of 7-methoxy-1-naphthylethyl benzene sulfonate (IV). The yield was 85%. The melting point was 85-86° C.

The data from IR, $^1$HNMR (CDCl$_3$) and MS were the same as provided in Example 1.

2) Synthesis of
N-[2-(7-methoxy-1-naphthyl)ethyl]phthalimide (II)

The compound IV (14 g, 0.041 mol) produced as described above and potassium phthalimide (9.3 g, 0.050 mol) were added into a reaction vessel, and acetonitrile (150 ml) was added. The mixture was heated and refluxed for 4 hours. After cooling it to room temperature, 200 ml of water was added, and the mixture was stirred and filtered. The filter cake formed was washed with water and dried, to produce 11.5 g of N-[2-(7-methoxy-1-naphthyl)ethyl]phthalimide (II). The yield was 85%. The melting point was 160-161° C.

The data from IR, $^1$HNMR (CDCl$_3$) and MS were the same as provided in Example 1.

Example 3

Preparation of
N-[2-(7-methoxy-1-naphthyl)ethyl]phthalimide (II)

1) Synthesis of 7-methoxy-1-naphthylethyl Benzene Sulfonate (IV)

7-methoxy-1-naphthyl ethanol (III, 7.7 g, 0.038 mol) was dissolved in 80 ml of pyridine, and a solution of benzenesulfonyl chloride (26.9 g, 0.152 mol) in pyridine was added dropwise over about one hour at 0° C. (exothermic). A reaction at a temperature of from −5° C. to 0° C. was allowed to proceed for 2 hours. The reaction solution was then poured into 150 g of ice water with stirring, and extracted with toluene (80 ml*3). The organic phases were combined, washed with water (200 ml*3), dried with magnesium sulfate, filtered to remove the drying agent, and concentrated under reduced pressure, to give an oil residue. The residue was recrystallized in 100 ml of ethanol, to produce 12 g of 7-methoxy-1-naphthylethyl benzene sulfonate (IV). The yield was 92%. The melting point was 85.5-87° C.

The data from IR, $^1$HNMR (CDCl$_3$) and MS were the same as provided in Example 1.

2) Synthesis of
N-[2-(7-methoxy-1-naphthyl)ethyl]phthalimide (II)

The compound IV (14 g, 0.041 mol) produced as described above and potassium phthalimide (10.8 g, 0.0574 mol) were added into a reaction vessel, and acetonitrile (150 ml) was added. The mixture was heated and refluxed for 4 hours. After cooling it to room temperature, 200 ml of water was added, and the mixture was stirred and filtered. The filter cake formed was washed with water and dried, to produce 12 g of N-[2-(7-methoxy-1-naphthyl)ethyl]phthalimide (II). The yield was 90%. The melting point was 160-160.9° C.

The data from IR, $^1$HNMR (CDCl$_3$) and MS were the same as provided in Example 1.

Example 4

Preparation of
N-[2-(7-methoxy-1-naphthyl)ethyl]phthalimide (II)

1) Synthesis of 7-methoxy-1-naphthylethyl Benzene Sulfonate (IV)

7-methoxy-1-naphthyl ethanol (III, 7.7 g, 0.038 mol) was dissolved in 100 ml of dichloroethane, and triethyl amine (7 ml) was added, and a solution of benzenesulfonyl chloride (40 g, 0.228 mol) in dichloroethane was added dropwise over about one hour at 0° C. A reaction at a temperature of from 10° C. to 15° C. was allowed to proceed for 1.5 hours. The reaction solution was then poured into 150 g of ice water with stirring, and extracted with dichloroethane (20 ml*3). The organic phases were combined, washed with water (100 ml*3), dried with magnesium sulfate, filtered to remove the drying agent, and concentrated under reduced pressure, to give an oil residue. The residue was recrystallized in 80 ml of methanol, to produce 11.8 g of 7-methoxy-1-naphthylethyl benzene sulfonate (IV). The yield was 89%. The melting point was 86.5-87.5° C.

The data from IR, $^1$HNMR (CDCl$_3$) and MS were the same as provided in Example 1.

2) Synthesis of
N-[2-(7-methoxy-1-naphthyl)ethyl]phthalimide (II)

The compound IV (14 g, 0.041 mol) produced as described above and potassium phthalimide (12.3 g, 0.0656 mol) were added into a reaction vessel, and dimethylformamide (200 ml) was added. The mixture was heated and refluxed for 2 hours. After cooling it to room temperature, 200 ml of water was added, and the mixture was stirred and filtered. The filter cake formed was washed with water and dried, to produce 12.3 g of N-[2-(7-methoxy-1-naphthyl)ethyl]phthalimide (II). The yield was 92.3%. The melting point was 160-161° C.

Example 5

Preparation of
N-[2-(7-methoxy-1-naphthyl)ethyl]phthalimide (II)

1) Synthesis of 7-methoxy-1-naphthylethyl Benzene Sulfonate (IV)

7-methoxy-1-naphthyl ethanol (III, 7.7 g, 0.038 mol) was dissolved in 100 ml of chloroform, and tripropyl amine (7 ml) was added, and a solution of methanesulfonyl chloride (35 g, 0.304 mol) in chloroform was added dropwise over about one hour at 0° C. A reaction at a temperature of from −5° C. to 0° C. was allowed to proceed for 1.5 hours. The reaction solution was then poured into 150 g of ice water with stirring, and extracted with dichloroethane (20 ml*3). The organic phases were combined, washed with water (100 ml*3), dried with magnesium sulfate, filtered to remove the drying agent, and concentrated under reduced pressure, to give an oil residue. The residue was recrystallized in 80 ml of methanol, to produce 10.8 g of 7-methoxy-1-naphthylethyl benzene sulfonate (IV). The yield was 83%. The melting point was 61.8-63° C. (in Literature [1], 62-63° C.).

The data from $^1$HNMR (CDCl$_3$) were the same as provided in Literature [1].

2) Synthesis of N-[2-(7-methoxy-1-naphthyl)ethyl]phthalimide (II)

The compound IV (14 g, 0.041 mol) produced as described above and potassium phthalimide (13 g, 0.0738 mol) were added into a reaction vessel, and dimethylformamide (200 ml) was added. The mixture was heated and refluxed for 2 hours. After cooling it to room temperature, 200 ml of water was added, and the mixture was stirred and filtered. The filter cake formed was washed with water and dried, to produce 11.9 g of N-[2-(7-methoxy-1-naphthyl)ethyl]phthalimide (II). The yield was 88%. The melting point was 160-161° C.

The data from IR, $^1$HNMR (CDCl$_3$) and MS were the same as provided in Example 1.

Example 6

Preparation of N-[2-(7-methoxy-1-naphthyl)ethyl] acetamide (I) (Agomelatine)

1) Synthesis of 2-(7-methoxy-1-naphthyl)ethylamine Hydrochloride (V)

N-[2-(7-methoxy-1-naphthyl)ethyl]phthalimide (II) (12.5 g, 0.038 mol) was dissolved in 1000 ml of ethanol, and 80% hydrazine hydrate (9.23 ml) was added. The mixture was heated and refluxed for 2 hours. After cooling to room temperature, it was filtered to remove the precipitated solid. The filtrate was concentrated till dry under reduced pressure, and 150 ml of dichloromethane was then added with stirring. The resulting solution was filtered to remove the undissolved substance and extracted with 3N HCl solution (100 ml*3). The filtrate was adjust to a pH of 11-12 by addition of 4N NaOH, and extracted with ethyl acetate (200 ml*3). The organic phases were combined, washed with water (100 ml*2), dried with magnesium sulfate, and filtered to remove the drying agent. The filtrate was concentrated to about half of the initial volume, and HCl/ethyl acetate was added to precipitate a solid. The solid was filtered off and dried, to produce 7.5 g of 2-(7-methoxy-1-naphthyl)ethylamine hydrochloride (V). The yield was 83.6%. The melting point was 214-215° C. (in Literature [2], 215° C.).

IR $\bar{v}_{cm^{-1}}$: 3424.90, 2665.73, 2620.00, 2540.06, 2464.52, 1526.51, 1601.34, 1576.24, 1510.09

$^1$HNMR (DMSO-d6) δ: 8.18 (s, 3H), 7.21 (dd, 1H, J=8.8, 2.4 Hz), 7.8 (d, 1H, J=9.2 Hz), 7.77 (d, 1H, J=8.0 Hz), 7.30 (t, 1H, J=8.4 Hz), 3.95 (s, 3H), 3.38 (t, 21-1, J=7.6 Hz), 3.1 (t, 2H, J=7.6 Hz)

MS: m/z 201 (M+1)

2) Synthesis of N-[2-(7-methoxy-1-naphthyl)ethyl] acetamide (I) (Agomelatine)

The compound V (6.0 g, 0.03 mol) produced as described above and sodium acetate (3.4 g) were dissolved in 70 ml of ethanol, and acetic anhydride (3.4 g, 0.033 mol) was added. The reaction solution was heated and refluxed for one hour. After cooling, about 100 ml of water was added, and the mixture was extracted with ethyl acetate (50 ml*3). The organic phases were combined, dried with anhydrous magnesium sulfate, and filtered to remove the drying agent. The filtrate was concentrated under reduced pressure, to give a solid. The solid was recrystallized in a 2:1 toluene/n-hexane mixture, to produce 5.3 g of agomelatine. The yield was 86.7%. The melting point was 107-109° C. (in Literature [2], 109° C.).

IR $\bar{v}_{cm^{-1}}$: 3249.97, 1552.65, 1640.57

$^1$HNMR (CDCl$_3$) δ: 7.77 (d, 1H, J=8.8 Hz), 7.16 (dd, 1H, J=8.8, 2.4 Hz), 7.47 (d, 1H, J=2.4 Hz), 5.55 (s, 1H), 3.99 (s, 3H), 3.65 (q, 21-1, J=6.8 Hz), 3.25 (t, 2H, CH2)

MS: m/z 243 (M+1)

Example 7

Preparation of N-[2-(7-methoxy-1-naphthyl)ethyl] acetamide (I) (Agomelatine)

1) Synthesis of 2-(7-methoxy-1-naphthyl)ethylamine Hydrochloride (V)

N-[2-(7-methoxy-1-naphthyl)ethyl]phthalimide (II) (12.5 g, 0.038 mol) was dissolved in 1000 ml of ethanol, and 2N aqueous NaOH solution (5 ml) was added. The mixture was heated and refluxed for 2 hours. After cooling to room temperature, it was filtered to remove the precipitated solid. The filtrate was concentrated till dry under reduced pressure, and 150 ml of dichloromethane was then added with stirring. The resulting solution was filtered to remove the undissolved substance and extracted with 3N HCl solution (100 ml*3). The filtrate was adjust to a pH of 11-12 by addition of 4N NaOH, and extracted with dichloroethane (200 ml*3). The organic phases were combined, washed with water (100 ml*2), dried with magnesium sulfate, and filtered to remove the drying agent. The filtrate was concentrated to about half of the initial volume, and HCl/ethyl acetate was added to precipitate a solid. The solid was filtered off and dried, to produce 6.9 g of 2-(7-methoxy-1-naphthyl)ethylamine hydrochloride (V). The yield was 76.9%. The melting point was 214-215° C. (in Literature [2], 215° C.).

The data from IR, $^1$HNMR (CDCl$_3$) and MS were the same as provided in Example 6.

2) Synthesis of N-[2-(7-methoxy-1-naphthyl)ethyl] acetamide (I) (Agomelatine)

The compound V (6.0 g, 0.03 mol) produced as described above and sodium acetate (3.4 g) were dissolved in 70 ml of ethanol, and acetic anhydride (3.4 g, 0.033 mol) was added. The reaction solution was heated and refluxed for one hour. After cooling, about 100 ml of water was added, and the mixture was extracted with ethyl acetate (50 ml*3). The organic phases were combined, dried with anhydrous magnesium sulfate, and filtered to remove the drying agent. The filtrate was concentrated under reduced pressure, to give a solid. The solid was recrystallized in a 2:1 toluene/n-hexane mixture, to produce 5.3 g of agomelatine. The yield was 86.7%. The melting point was 108-109° C. (in Literature [2], 109° C.).

Example 8

Preparation of N-[2-(7-methoxy-1-naphthyl)ethyl] acetamide (I) (Agomelatine)

1) Synthesis of 2-(7-methoxy-1-naphthyl)ethylamine Hydrochloride (V)

N-[2-(7-methoxy-1-naphthyl)ethyl]phthalimide (II) (12.5 g, 0.038 mol) was dissolved in 1000 ml of ethanol, and 2N aqueous KOH solution (5 ml) was added. The mixture was heated and refluxed for 2 hours. After cooling to room temperature, it was filtered to remove the precipitated solid. The filtrate was concentrated till dry under reduced pressure, and 150 ml of dichloromethane was then added with stirring. The resulting solution was filtered to remove the undissolved substance and extracted with 2N sulfuric acid solution (100 ml*3). The filtrate was adjust to a pH of 11-12 by addition of 4N KOH, and extracted with dichloromethane (150 ml*3). The organic phases were combined, washed with water (100 ml*2), dried with magnesium sulfate, and filtered to remove the drying agent. The filtrate was concentrated to about half of the initial volume, and HCl/ethyl acetate was added to precipitate a solid. The solid was filtered off and dried, to produce 6.7 g of 2-(7-methoxy-1-naphthyl)ethylamine hydrochloride (V). The yield was 74.7%. The melting point was 214-215° C. (in Literature [2], 215° C.).

The data from IR, $^1$HNMR (CDCl$_3$) and MS were the same as provided in Example 6.

2) Synthesis of N-[2-(7-methoxy-1-naphthyl)ethyl] acetamide (I) (Agomelatine)

The compound V (6.0 g, 0.03 mol) produced as described above and potassium carbonate (5 g) were added to 20 ml of water and 40 ml of dichloromethane, and stirred for 30 minutes. The aqueous layer was removed. The organic layer was cooled to the temperature of 0° C., and acetyl chloride (7.8 g, 0.1 mol) was added dropwise. A reaction was allowed to proceed at room temperature for 1 hour. 100 ml water was then added, and the reaction solution was extracted with dichloromethane (50 ml*3). The organic phases were combined, dried with anhydrous magnesium sulfate, and filtered to remove the drying agent. The filtrate was concentrated under reduced pressure, to give a solid. The solid was recrystallized in a 2:1 toluene/n-hexane mixture, to produce 4.8 g of agomelatine. The yield was 78.5%. The melting point was 107-108° C. (in Literature [2], 109° C.).

The data from IR, $^1$HNMR (CDCl$_3$) and MS were the same as provided in Example 6.

REFERENCES

Literature [1]: Leclerc, Veronique; Fourmaintraux, Eric; Depreux, Patrick; Lesieur, Daniel; Morgan, Peter; et al.; BMECEP; Bioorganic & Medicinal Chemistry; English; 6; 10; 1998; 1875-1888

Literature [2]: Patrick Depreux, Daniel Lesieur, Hamid At Mansour, et al, Synthesis and Structure-Activity Relationships of Novel Naphthalenic and Bioisosteric Related Amidic Derivatives as Melatonin Receptor Ligands, Journal of Medicinal Chemistry, 1994, Vol. 37, No. 20: 3236

What is claimed is:

1. An N-[2-(7-methoxy-1-naphthyl)ethyl] phthalimide of formula II:

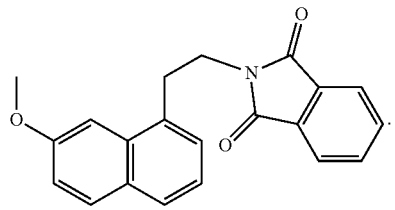

2. A process for the manufacture of N-[2-(7-methoxy-1-naphthyl)ethyl] phthalimide of formula II,

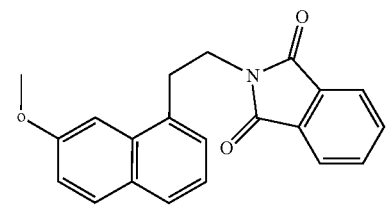

the process comprising the step of reacting 7-methoxy-1-naphthylethyl alkyl- or aryl-sulfonate, wherein the alkyl is a linear or branched $C_1$-$C_6$ alkyl, and the aryl is a $C_5$-$C_6$ aryl unsubstituted or substituted by a linear or branched $C_1$-$C_6$ alkyl or a linear or branched $C_1$-$C_6$ alkoxy, with potassium phthalimide in a polar aprotic solvent.

3. The process according to claim 2, wherein the 7-methoxy-1-naphthylethyl alkyl- or aryl-sulfonate is obtained by reacting 7-methoxy-1-naphthyl ethanol with an alkyl- or aryl-sulfonyl halide, wherein the alkyl is a linear or branched $C_1$-$C_6$ alkyl, and the aryl is a $C_5$-$C_6$ aryl unsubstituted or substituted by a linear or branched $C_1$-$C_6$ alkyl or a linear or branched $C_1$-$C_6$ alkoxy, in an aprotic solvent in the presence of a base.

4. The process according to claim 3, wherein the alkyl- or aryl-sulfonyl halide is an alkyl- or aryl-sulfonyl chloride.

5. The process according to claim 3, wherein the base is selected from $NR_3$, wherein R is identical or different and represents H or a linear or branched $C_1$-$C_4$ alkyl, with a proviso that all the R groups are not simultaneously H, or pyridine and is preferably selected from diethyl amine, dipropyl amine, dibutyl amine, triethyl amine, tripropyl amine, tributyl amine, or pyridine.

6. The process according to claim 3, wherein the aprotic solvent is partially chlorinated $C_1$-$C_6$ alkane, fully chlorinated $C_1$-$C_6$ alkane or pyridine.

7. The process according to claim 2, wherein the polar aprotic solvent is selected from dimethylformamide or acetonitrile.

8. A process for the manufacture of 2-(7-methoxy-1-naphthyl)ethylamine or its salt, the process comprising the steps of alkaline hydrolysis of N-[2-(7-methoxyl-1-naphthyl)ethyl] phthalimide, and optionally forming a salt with an acid.

9. A process for the manufacture of agomelatine, the process comprising the following steps:
1) subjecting N-[2-(7-methoxy-1-naphthyl)ethyl] phthalimide to alkaline hydrolysis in a linear or branched $C_1$-$C_4$ alkanol, and optionally forming a salt with an acid, to give 2-(7-methoxy-1-naphthyl)ethylamine or its salt; and
2) reacting 2-(7-methoxy-1-naphthyl)ethylamine or its salt with an acylating agent, to produce agomelatine.

10. The process according to claim 9, wherein the alkanol is methanol, ethanol, isopropanol, n-butanol, or a combination thereof.

11. The process according to claim 9, wherein the alkaline hydrolysis is carried out using an alkali metal hydroxide, an alkaline-earth metal hydroxide or hydrazine hydrate.

12. The process according to claim 9, wherein, after alkaline hydrolysis, the obtained hydrolyzate is purified by extraction with a nonpolar organic solvent.

13. The process according to claim 9, wherein the acylating agent is acetic anhydride or acetyl chloride.

14. The process according to claim 4, wherein the alkyl-sulfonyl chloride is $C_1$-$C_4$ alkyl-sulfonyl chloride.

15. The process according to claim 4, wherein the aryl-sulfonyl chloride is benzenesulfonyl chloride, with the benzene being unsubstituted or substituted by a linear or branched $C_1$-$C_6$ alkyl or a linear or branched $C_1$-$C_6$ alkoxy.

16. The process according to claim 15, wherein the aryl-sulfonyl chloride is benzenesulfonyl chloride, with the benzene being unsubstituted or substituted by a linear or branched $C_1$-$C_4$ alkyl or a linear or branched $C_1$-$C_4$ alkoxy.

17. The process according to claim 15, wherein the aryl-sulfonyl chloride is benzenesulfonyl chloride or p-toluenesulfonyl chloride.

18. The process according to claim 5, wherein the base is selected from the group consisting of diethyl amine, dipropyl amine, dibutyl amine, triethyl amine, tripropyl amine, tributyl amine and pyridine.

19. The process according to claim 6, wherein the aprotic solvent is selected from the group consisting or dichloromethane, dichloroethane, chloroform and carbon tetrachloride.

20. The process according to claim 8, wherein the acid is a solution of hydrogen chloride in ethyl acetate.

21. The process according to claim 11, wherein the alkaline hydrolysis is carried out using sodium hydroxide, potassium hydroxide or hydrazine hydrate.

22. The process according to claim 12, wherein the nonpolar organic solvent is a partially chlorinated $C_1$-$C_6$ alkane, a fully chlorinated $C_1$-$C_6$ alkane or ethyl acetate.

23. The process according to claim 22, wherein the nonpolar organic solvent is selected from the group consisting or dichloromethane, dichloroethane, chloroform, carbon tetrachloride and ethyl acetate.

* * * * *